US011560399B2

(12) United States Patent
Arefyev et al.

(10) Patent No.: US 11,560,399 B2
(45) Date of Patent: Jan. 24, 2023

(54) PROCESS FOR PREPARING MANNOSE DERIVATIVES

(71) Applicant: ENTEROME, Paris (FR)

(72) Inventors: Denis Viktorovich Arefyev, Florence, SC (US); Michael P. Cruskie, Florence, SC (US); Chaminda Priyapushpa Gamage, Florence, SC (US); Joseph Chase Chewning, Lamar, SC (US); Marc Labelle

(73) Assignee: ENTEROME, Paris (FR)

( * ) Notice: Subject to any disclaimer, the term of this patent is extended or adjusted under 35 U.S.C. 154(b) by 0 days.

(21) Appl. No.: 17/263,012

(22) PCT Filed: Jul. 26, 2019

(86) PCT No.: PCT/EP2019/070276
§ 371 (c)(1),
(2) Date: Jan. 25, 2021

(87) PCT Pub. No.: WO2020/021113
PCT Pub. Date: Jan. 30, 2020

(65) Prior Publication Data
US 2021/0309682 A1    Oct. 7, 2021

(30) Foreign Application Priority Data
Jul. 26, 2018    (EP) .................................... 18306013

(51) Int. Cl.
*C07H 1/06* (2006.01)
*C07H 7/06* (2006.01)

(52) U.S. Cl.
CPC .............. *C07H 1/06* (2013.01); *C07H 7/06* (2013.01)

(58) Field of Classification Search
None
See application file for complete search history.

(56) References Cited

U.S. PATENT DOCUMENTS

2005/0222048 A1   10/2005   Tsuji et al.
2014/0243283 A1*  8/2014    Ramtohul .......... A61K 31/7034
                                                514/23

FOREIGN PATENT DOCUMENTS

WO    WO 2014/100158 A1    6/2014
WO    WO 2018/199105 A1    12/2016

OTHER PUBLICATIONS

Teledyne Isco, Inc., Strategies to Purify Carbohydrate Based Compounds with Flash Chromatography, Chromatography Note ANM75, dated Nov. 9, 2021. (Year: 2021).*

Extended European Search Report for European Application No. 18306013.6, dated Oct. 25, 2018.
International Search Report for International Application No. PCT/EP2019/070276, dated Oct. 21, 2019.
Leaver et al., "X-Ray Crystal Structure Determinations of Galactosylacetylene Building Blocks," Journal of Carbohydrate Chemistry, vol. 29, No. 8-9, 2010 (Available online Mar. 15, 2011), pp. 379-385.
Lubin-Germain et al., "Direct C-Glycosylation by Indium-Mediated Alkynylation on Sugar Anomeric Position," Organic Letters, vol. 10, No. 5, 2007 (Available online Feb. 6, 2008), pp. 725-728.
Man et al., "The role of bacteria and pattern-recognition receptors in Crohn's disease," Nature Reviews Gastroenterology and Hepatology, vol. 8, No. 3, 2011 (Available online Feb. 8, 2011 and corrected online Mar. 18, 2021), pp. 152-168.
Stichler-Bonaparte et al. "Oligosaccharide Analogues of Polysaccharides, Part 23, Synthesis of a Dimeric Acetvieno Cyclodextrin from a Mannopyranose-Derived Dialkyne." Helvetica Chimica Acta, vol. 84, No. 8, Aug. 15, 2001, pp. 2355-2367.

* cited by examiner

*Primary Examiner* — Layla D Berry
(74) *Attorney, Agent, or Firm* — Birch, Stewart, Kolasch & Birch, LLP

(57) ABSTRACT

The invention relates to a process to prepare a compound of the following formula (I): (I), in which P represents a protective group of a hydroxyl function which is a —COR$^1$ group with R$^1$ representing an aryl or a (C$_1$C$_6$)alkyl, R represents a hydrogen atom or a protective group of a terminal alkyne, from mannose, comprising the following steps: (a) protecting the 5 hydroxyl groups of the mannose by a protective group P; (b) coupling the protected mannose obtained at step (a) with a compound of the following formula (II). The present invention also relates to a compound of formula (IIIa).

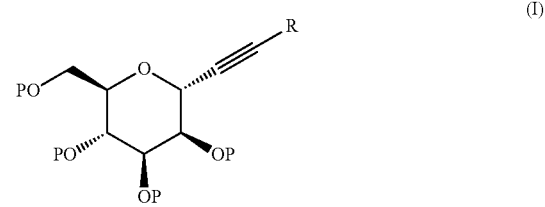

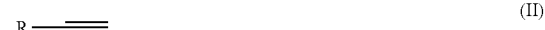

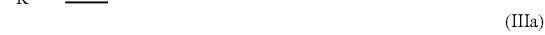

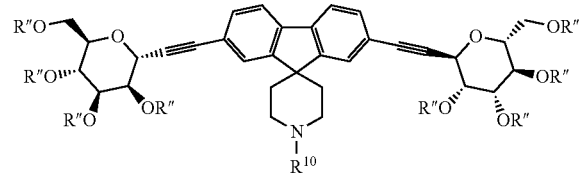

19 Claims, 2 Drawing Sheets

PROCESS FOR PREPARING MANNOSE DERIVATIVES

FIELD OF THE INVENTION

The present invention provides a process for preparing mannose derivatives and their intermediates which are useful for the treatment or prevention of bacterial infections, such as urinary tract infection (UTI) and inflammatory bowel disease (IBD).

STATE OF THE ART

Inflammatory bowel disease (IBD) is a complex chronic inflammatory disorder, with the two more common forms being ulcerative colitis (UC) and Crohn's disease (CD). IBD is a multifactorial disease that results from a combination of predisposing genetic factors, environmental triggers, dysbiosis of the gastrointestinal microbiota and an inappropriate inflammatory response (Man et al., 2011, Nat Rev Gastroenterol Hepatol, March, 8(3):152-68).

Several pathogens have been proposed as causative agents. In particular, adherent-invasive *E. coli* (AIEC) has been reported to be more prevalent in CD patients than in controls. It has also been demonstrated recently that FimH antagonists are potentially effective in treating urinary tract infections.

WO 2014/100158 and WO 2016/199105 describe mannose derivatives which are useful for the treatment or prevention of bacterial infections, in particular urinary tract infection, inflammatory bowel disease, ulcerative colitis or Crohn's disease.

As mannose derivatives are of particular interest for use in pharmaceutical industry, it is necessary to be able to synthesize these compounds efficiently on a large scale and at low cost with a minimum of steps and good yields.

In WO 2014/100158 and WO 2016/199105, mannose derivatives which comprise a triple bond on the anomeric position of mannose are of particular interest. They are synthesized by Sonogashira coupling between compound (I') and an aromatic (di)halide (see FIG. 1). In particular, three intermediates (I'a), (I'b) and (I'c) are used (see FIG. 2).

The synthesis of compounds (I'a) and (I'b) is described in Vasella and coll. *Helvetica Chimica Acta* 2001, 84, 2355-2367. Compounds (I'a) and (I'b) are obtained in 3 and 4 steps successively starting from 1,6-anhydro-β-D-mannopyranose (A), which is not readily available and requires a multistep synthesis.

Compound (I'c) is obtained in 3 steps from 2,3,4,6-Tetra-O-benzyl-D-mannopyranose (B), which is not readily available and requires a multistep synthesis.

In an article from Lubin-Germain and coll. *Org. Lett.* 2008, 10, 725-728, compound (I'd) is obtained by alkynylation of 1,4,6-tri-O-acetyl-2,3-O-isopropylidene-D-mannopyranoside (C). This starting material is not commercially available and its synthesis requires multiple steps of protection/deprotection from mannose. Additionally, the alkynyl iodide used is substituted with a phenyl which cannot be removed and alkynyl iodide is usually more expensive than terminal alkynes.

In general, alkynylation of carbohydrate derivatives has also been described using organotin acetylides (for example with glucose derivatives in US 2005/222048). However, tin reagents are toxic and their use is avoided in pharmaceutical industry. Additionally, the glucose derivative used as starting material is obtained through several steps of protection/deprotection.

To this extent, a need remains for the development of a process to synthesize compounds of formula (I) more efficiently on a large scale, at low cost, with a minimum of steps, good yields and starting from readily available and cheap starting material.

Similarly, it is necessary to develop an efficient process to prepare compounds of formula (III) and of formula (V) which are mannose derivatives useful for the treatment or prevention of bacterial infections.

SUMMARY OF THE INVENTION

The present invention relates to a process to prepare a compound of the following formula (I):

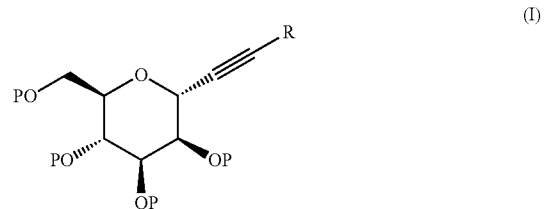

in which

P represents a protective group of a hydroxyl function which is a —$COR^1$ group with $R^1$ representing an aryl or a ($C_1$-$C_6$)alkyl, R represents a hydrogen atom or a protective group of a terminal alkyne, from mannose, comprising the following steps:

(a) protecting the 5 hydroxyl groups of the mannose by a protective group P;

(b) coupling the protected mannose obtained at step (a) with a compound of the following formula (II)

In particular, the protective group P is a —$COR^1$ group with $R^1$ representing an aryl group, preferably a phenyl group.

Preferably, R is a —$SiR^2R^3R^4$ group with $R^2$, $R^3$ and $R^4$ representing independently from each other a ($C_1$-$C_6$)alkyl group or a biphenyl group, preferably $R^2$, $R^3$ and $R^4$ represent a methyl group.

Advantageously, step b) is performed in the presence of a base, an alkylaluminum halide and optionally a Lewis acid, preferably in the presence n-Butyl lithium, diethyl aluminium chloride and aluminium chloride.

Preferably, step (b) is divided into three sub-steps:

(b1) deprotonation of the compound of formula (II) with a base, (b2) addition of an alkylaluminium halide, preferably diethyl aluminium chloride, (b3) coupling the product obtained at step (a) with the product of step (b2) in the presence of a Lewis acid, preferably aluminium chloride.

The invention also relates to a process to prepare a compound of formula (III):

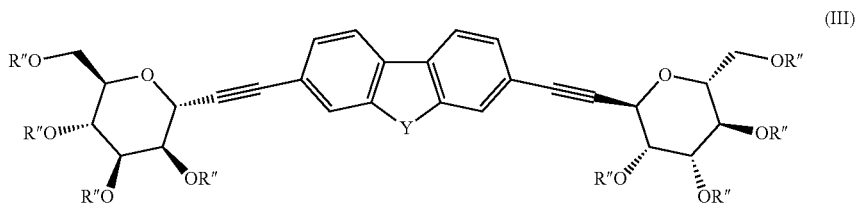

(III)

in which
Y represents a group

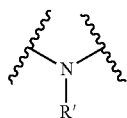

or a group B

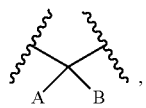

with A and B representing independently of each other a hydrogen, a hydroxyl, an amine or a radical selected from a $(C_1-C_6)$alkyl and an aryl, said radical being substituted or not by a $(C_1-C_6)$alkyl, a 3-8 membered ring cycloalkyl, —$OR^5$, —$OC(O)R^5$ or —$COOR^5$, $R^5$ representing a hydrogen or a $(C_1-C_6)$alkyl,
or A and B form together with the carbon atom to which they are bound a 3-7 membered saturated monocyclic ring having 0, 1 or 2 heteroatoms selected from O, N and S, one or several carbon or nitrogen of the ring being optionally substituted by an oxo, a $(C_1-C_6)$alkyl, —$OR^6$, —$NR^6R^7$, —$SO_2R^6$—$C(O)R^6$ or —$C(O)OR^6$, with $R^6$ and $R^7$ representing independently a hydrogen or a radical selected from a $(C_1-C_6)$alkyl, an aryl, a heteroaryl, a 3-8 membered ring cycloalkyl and a 3-8 membered ring heterocycloalkyl, said radical being optionally substituted by a $(C_1-C_6)$ alkyl, an aryl, a heteroaryl, a 3-8 membered ring cycloalkyl or a 3-8 membered ring heterocycloalkyl, a halogen, —$NR^8R^9$, —CN, —$C(O)OR^8$, —$C(O)NR^8R^9$ or —$OR^8$, with $R^8$ and $R^9$ being independently a hydrogen atom or a $(C_1-C_6)$ alkyl, or $R^8$ and $R^9$ form together with the nitrogen to which they are bound a 3-8 membered ring heterocycloalkyl,
with R' representing a hydrogen atom or a radical selected from a $(C_1-C_6)$ alkyl, an aryl, a 3-8 membered ring cycloalkyl and a 3-8 membered ring heterocycloalkyl, said radical being optionally substituted by a $(C_1-C_6)$ alkyl, a 3-8 membered ring cycloalkyl, a 3-8 membered ring heterocycloalkyl, —$C(O)OR^a$, —$C(O)NR^aR^b$ or —$OR^a$, with $R^a$ and $R^b$ being independently a hydrogen atom or a $(C_1-C_6)$ alkyl optionally substituted by a 3-8 membered ring heterocycloalkyl, or $R^a$ and $R^b$ form together with the nitrogen a 3-8 membered ring heterocycloalkyl,
R'' represents a hydrogen atom or a protective group of a hydroxyl function which is a —$COR^1$ group with $R^1$ representing an aryl or a $(C_1-C_6)$alkyl,
from mannose, comprising the following steps:
(a)(b) performing steps (a) and (b) to obtain the compound of formula (I) as described above;
(c) optionally deprotecting the terminal alkyne of the compound obtained after steps (a)(b) to obtain compound of formula (I) in which R=H;
(d) Sonogashira coupling of the compound obtained at steps (a)(b) or when applicable at step (c) with a compound of the following formula (IV):

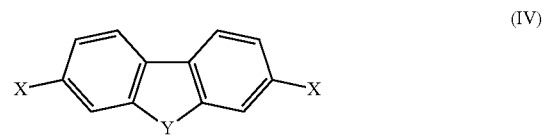

(IV)

in which X is a halogen atom;
(e) optionally deprotecting the hydroxyl groups protected by a group P to obtain compound of formula (III) in which R''=H;
(f) recovering the compound of formula (III) obtained at step (d) or when applicable at step (e).
In particular, the compound of formula (III) is a compound of formula (IIIa)

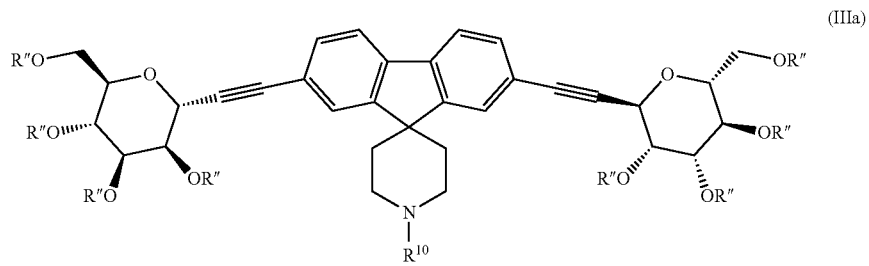

(IIIa)

advantageously obtained from compound (IVa)

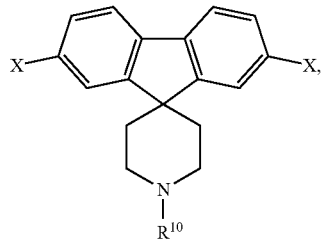
(IVa)

with R¹⁰ representing a hydrogen, a $(C_1-C_6)$alkyl, —SO$_2$R⁶, —C(O)R⁶ or —C(O)OR⁶, with R⁶, R" and X being as described above.

Advantageously, R¹⁰ is a —C(O)R⁶ group with R⁶ representing an aryl or a $(C_1-C_6)$alkyl, preferably R⁶ is a methyl group.

Preferably, steps (c) and (d) occur in a one-pot process.

In particular, compound of formula (IVa)

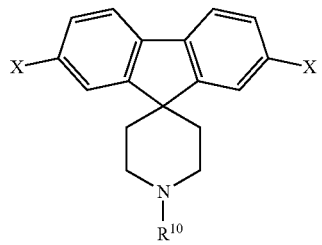
(IVa)

is a compound of formula (IVa) wherein R¹⁰ and is a —COMe group and is obtained from compound of formula (IVa) with R¹⁰ being a protective group of an amine function different from —COMe by deprotection and acetylation in a one-pot process.

The invention also relates to a process to prepare a compound of formula (V):

(V)

in which
R¹¹ represents:
a —CONR¹²R¹³ group with R¹² and R¹³ representing independently a hydrogen, a $(C_1-C_6)$alkyl or R¹² and R¹³ form together with the nitrogen a 3-8 membered ring heterocycloalkyl or cycloalkyl a radical selected from a cycloalkenyl, an aryl and a heteroaryl, said radical being substituted or not by a $(C_1-C_6)$ alkyl, an aryl, a heteroaryl, a halogen, —C(O)OR$^a$,
—C(O)NR$^a$R$^b$, —SO$_2$R$^a$, —SO$_2$NR$^a$R$^b$, —NR$^a$R$^b$, —OR$^a$, —CN or —NO$_2$, with R$^a$ and R$^b$ being independently a hydrogen atom or a $(C_1-C_6)$ alkyl, R" represents a hydrogen atom or a protective group of a hydroxyl function which is a —COR¹ group with R¹ representing an aryl or a $(C_1-C_6)$alkyl, from mannose, comprising the following steps:
(a)(b) performing steps (a) and (b) to obtain the compound of formula (I) as described above;
(c) optionally deprotecting the terminal alkyne of the compound obtained after steps (a)(b) to obtain compound of formula (I) in which R=H;
(d) Sonogashira coupling of the compound obtained at steps (a)(b) or when applicable at step (c) with a compound of the following formula (VI):

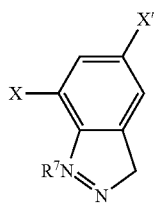
(VI)

in which X is a halogen atom and X' is a halogen or a radical R¹¹;
(e) optionally deprotecting the hydroxyl groups protected by a group P to obtain compound of formula (V) in which R"=H;
(f) recovering the compound of formula (V) obtained at step (d) or when applicable at step (e).

Advantageously, R¹¹ is a pyridinone substituted or not by a $(C_1-C_6)$ alkyl.

Preferably, the compound of formula (V) is a compound of formula (Va)

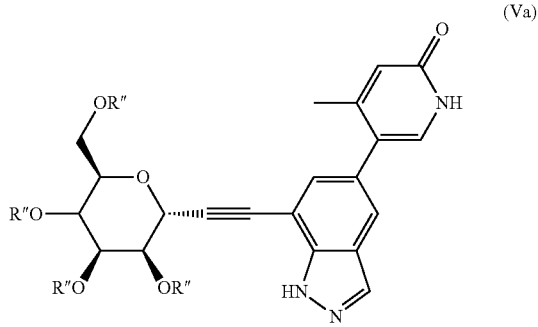
(Va)

In particular, steps (c) and (d) occur in a one-pot process.

The present invention also relates to a compound of formula (IIIa):

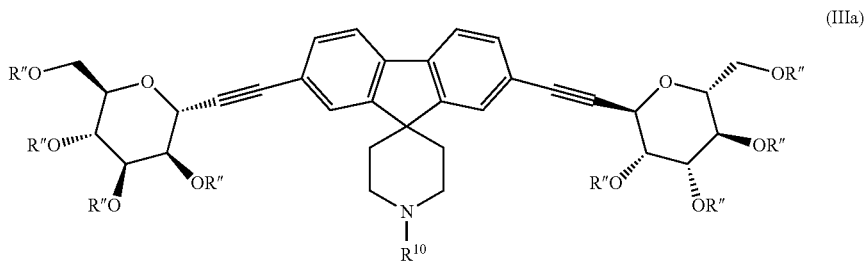

(IIIa)

wherein $R^{10}$ represents a hydrogen, a $(C_1-C_6)$alkyl, $-SO_2R^6$, $-C(O)R^6$ or $-C(O)OR^6$, with $R^6$ being a hydrogen or a radical selected from a $(C_1-C_6)$alkyl, an aryl, a heteroaryl, a 3-8 membered ring cycloalkyl and a 3-8 membered ring heterocycloalkyl, said radical being optionally substituted by a $(C_1-C_6)$ alkyl, an aryl, a heteroaryl, a 3-8 membered ring cycloalkyl or a 3-8 membered ring heterocycloalkyl, a halogen, $-NR^8R^9$, $-CN$, $-C(O)OR^8$, $-C(O)NR^8R^9$ or $-OR^8$, with $R^8$ and $R^9$ being independently a hydrogen atom or a $(C_1-C_6)$ alkyl, or $R^8$ and $R^9$ form together with the nitrogen to which they are bound a 3-8 membered ring heterocycloalkyl, and R" represents $-COR^1$ group with $R^1$ being an aryl or a $(C_1-C_6)$alkyl.

FIGURES

DETAILED DESCRIPTION OF THE INVENTION

Figure 1:
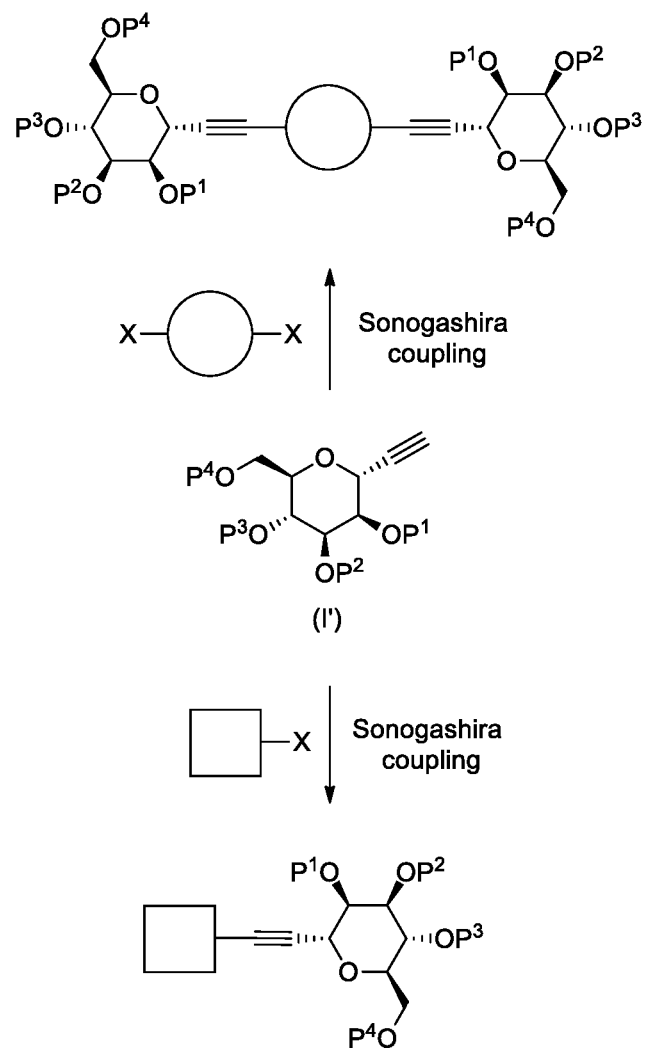
FIG. 1 illustrates the synthesis of mannose derivatives as described in WO 2014/100158 and WO 2016/199105 via Sonogashira coupling starting from compound (I') with R=H, and $P^1$, $P^2$, $P^3$ and $P^4$ are protective groups of hydroxyl function.
Figure 2:
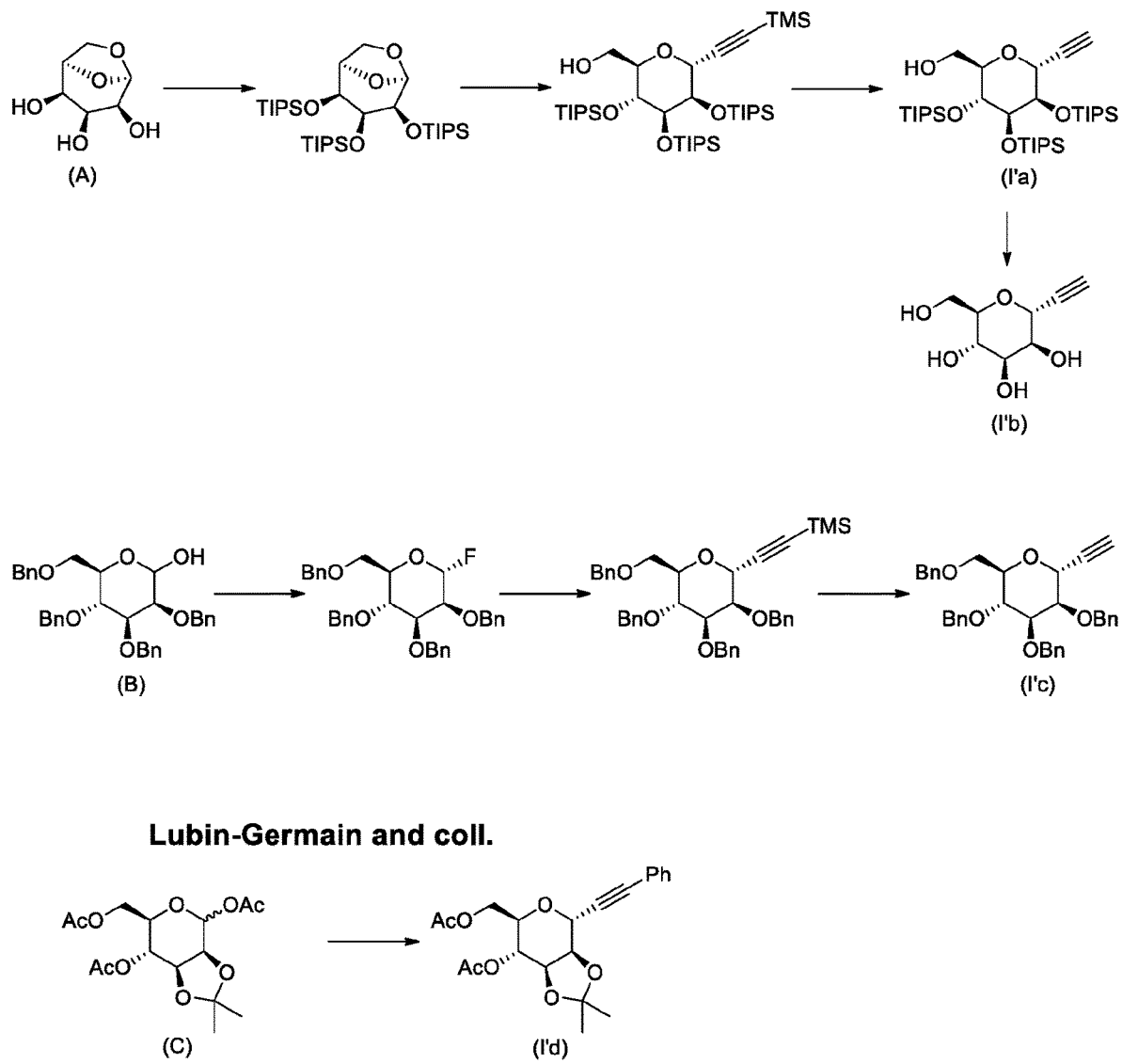
FIG. 2 illustrates the synthetic routes for the preparation of compounds of formula (I') such as compounds (I'a), (I'b) and (I'c) according to the prior art.

The applicants have developed a process to prepare mannose derivatives which are useful for the treatment or prevention of bacteria infections, such as urinary tract infection (UTI) and inflammatory bowel disease (IBD).

In particular, the process comprise the preparation of biologically active compounds of formula (III) or (V), and preparation of key intermediates such as compounds of formula (I).

The process developed by the applicants is adapted for preparation on an industrial scale of active compounds of formula (III) or (V) and present numerous advantages:
- compounds of formula (I) are obtained in a limited number of steps from a cheap commercially available reagent, i.e. mannose;
- the synthetic route does not require chiral synthesis since the chiral centres are contained in the starting reagent;
- the operating conditions are mild and do not use toxic reagents like organotin;
- the product is obtained with high chiral purity as chirality is controlled since starting material selection as per Mannose specifications and Chirality is assessed through current HPLC method.
- the global yield of the synthetic route starting from mannose and leading to compound of formula (IIIa)-3 is 35% to 40%.

Definitions

The term "halogen", as used in the present invention, refers to a fluorine, bromine, chlorine or iodine atom.

The term "$(C_1-C_6)$alkyl", as used in the present invention, refers to a saturated straight or branched hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "$(C_2-C_6)$alkenyl", as used in the present invention, refers to an unsaturated straight or branched hydrocarbon chain containing from 2 to 6 carbon atoms comprising at least one carbon-carbon double bond including, but not limited to, ethenyl, n-propenyl, iso-propenyl, n-butenyl, n-pentenyl, n-hexenyl, and the like.

The term "aryl", as used in the present invention, refers to an aromatic hydrocarbon group comprising preferably 6 to 10 carbon atoms and comprising one or several fused rings, such as, for example, a phenyl or naphtyl group. Advantageously, it is a phenyl group.

The term "heteroaryl" as used in the present invention refers to an aromatic heterocycle as defined above. It can be is more particularly an aromatic monocyclic or bicyclic heterocycle, each cycle comprising 5 or 6 members, such as a pyrrole, a furane, a thiophene, a thiazole, an isothiazole, an oxazole, an isoxazole, an imidazole, a pyrazole, a triazole, a pyridine, a pyrimidine, a pyridazine, a pyrazine, a triazine (such as 1, 3, 5-triazine), an indole, a benzofurane, a benzothiophene, a benzothiazole, a benzoxazole, a benzimidazole, an indazole, a benzotriazole, a quinoline, an isoquinoline, a quinazoline or a quinoxaline.

The term "cycloalkyl" as used in the present invention refers to a saturated mono-, bi- or tri-cyclic alkyl group as defined above comprising between 3 and 12 carbon atoms. It also includes fused, bridged or spiro-connected cycloalkyl groups. The term "cycloalkyl" includes, but is not limited to, cyclopropyl, cyclobutyl, cyclopentyl, cyclohexyl or adamantyl.

The term "heterocycloalkyl" as used in the present invention refers to saturated cycloalkyl group as defined above further comprising at least one heteroatom such as nitrogen, oxygen or sulphur. The term "heterocycloalkyl" includes, but is not limited to, pyranyl, piperidyl, piperidinyl, piperazinyl, 1,4-dioxanyl, morpholinyl, tetrahydrofuranyl, oxetanyl, pyrrolidinyl or pyrrolidyl.

The term "cycloalkenyl" as used in the present invention refers to unsaturated mono- or bi-cyclic alkenyl group as defined above comprising between 3 and 12 carbon atoms. The term "cycloalkenyl" includes, but is not limited to, cyclopropenyl, cyclobutenyl, cyclopentenyl or cyclohexenyl.

The term "oxo" as used in the present invention refers to the functional group '═O' (a substituent oxygen atom connected to another atom by a double bond).

Protective groups of amine function are well known to persons skilled in the art. These groups protect the amine functions of undesirable reactions. For example, a chemical reaction can be performed selectively at another reactive site which is not protected. The protective groups of the amine functions can be such as those described in "Protective Groups In Organic synthesis", (John Wiley & Sons, New York (1981)) and Harrison et al. "Compendium of Synthetic Organic Methods", Vols. 1 to 8 (J. Wiley & Sons, 1971 to 1996). The protective groups of amine functions comprise carbamates, amides, amino acetal derivatives, N-benzyl derivatives, imine derivatives and N-heteroatom derivatives. In particular, they can be selected from among acetyl, benzoyl, pivaloyl, phenylsulfonyl, benzyl (Bn), t-butyloxycarbonyl (Boc), benzyloxycarbonyl (Cbz), p-methoxybenzyloxycarbonyl, p-nitrobenzyl-oxycarbonyl, trichloroethoxycarbonyl (TROC), allyloxycarbonyl (Alloc), 9-Fluorenylmethyloxycarbonyl (Fmoc), trifluoro-acetyl and benzyl carbamates (substituted or unsubstituted) and the like. Preferably, a protective group of amine function is a Boc group or an acetyl group.

Protective groups of hydroxyl function are well known to those skilled in the art. These groups protect the hydroxyl functions against undesirable reactions. The protective groups of hydroxyl functions can be such as described in Greene, "Protective Groups In Organic synthesis", (John Wiley & Sons, New York (1981)) and Harrison et al. "Compendium of Synthetic Organic Methods", Vols. 1 to 8 (J. Wiley & Sons, 1971 to 1996). The protective groups of hydroxyl functions comprise substituted or unsubstituted methyl or alkyl ethers or esters e.g. methoxymethyl, benzyloxymethyl, 2-methoxyethoxymethyl, 2-(trimethylsilyl) ethoxymethyl, t-butyl, benzyl and triphenylmethyl, benzyl ethers (substituted or unsubstituted), tetrahydropyranyl ethers, allyl ethers, substituted ethyl ethers e.g. 2,2,2-trichloroethyl, silyl ethers or alkylsilyl ethers, e.g. trimethylsilyl, t-butyldimethylsilyl and t-butyldiphenylsilyl, heterocycle ethers; and esters prepared by reaction of the hydroxyl group with a carboxylic acid e.g. tert-butyl, benzyl or methyl esters, carbonates in particular benzyl or halogenoalkyl carbonate, acetate, propionate, benzoate and the like.

Protective groups of a terminal alkyne are well known to those skilled in the art. These groups protect the terminal alkyne functions against undesirable reactions. The protective groups of terminal alkyne functions can be such as described in Greene, "Protective Groups In Organic synthesis", (John Wiley & Sons, New York (1981)) and Harrison et al. "Compendium of Synthetic Organic Methods", Vols. 1 to 8 (J. Wiley & Sons, 1971 to 1996). The protective groups of terminal alkyne functions comprise silyl groups such as a —SiR²R³R⁴ group with R², R³ and R⁴ representing independently from each other a ($C_1$-$C_6$)alkyl group or a biphenyl group.

The term "alkylaluminum halide" as used in the present invention refers to a compound of formula $R^a_n AlX_{3-n}$ with $R^a$ representing a ($C_1$-$C_6$)alkyl group, n being a whole number between 1 and 2 and X representing a halogen.

The expression "room temperature" designates typically a temperature ranging from 18° C. to 25° C.

The term "one-pot process", as used in the present invention, refers to a process wherein a reactant is subjected to successive chemical reactions in just one reactor.

Preparation of Compounds of Formula (I)

The invention deals with a process to prepare a compound of the following formula (I):

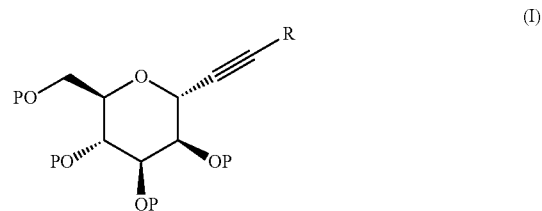

(I)

in which:

P represents a protective group of a hydroxyl function which is a —COR¹ group with R¹ representing an aryl group or a ($C_1$-$C_6$)alkyl group, R represents a hydrogen atom or a protective group of a terminal alkyne, from mannose, comprising the following steps:
(a) protecting the 5 hydroxyl groups of the mannose by a protective group P;
(b) coupling the protected mannose obtained at step (a) with a compound of the following formula (II)

(II)

Preferably, the protective group P is a —COR¹ group with R¹ representing an aryl group, preferably R¹ is a phenyl group.

In particular, R is a —SiR²R³R⁴ group with R², R³ and R⁴ representing independently from each other a ($C_1$-$C_6$)alkyl group or a biphenyl group, preferably R², R³ and R⁴ represent a methyl group.

Step (a)—Protection Step

Protecting the 5 hydroxyl groups of the mannose by a protective group P can be obtained by esterification of mannose.

Esterification can be conducted under conditions well known to skilled persons.

Notably, mannose can react with a carboxylic acid or its derivatives such as an anhydride acid or an acyl chloride.

In particular, mannose reacts with acyl chloride, notably benzoyl chloride (BzCl), in the presence of a base.

Advantageously, the reaction occurs in the presence of at least 6 molar equivalents of acyl chloride, more advantageously between 6 and 10 molar equivalents.

In particular, the base is an amine, notably triethylamine (TEA), diisopropylethylamine (DIPEA), piperidine or pyridine. Preferably, the base is pyridine.

Advantageously, the base is the solvent.

The protection reaction can be catalysed by a catalyst such as dimethylaminopyridine (DMAP).

Preferably, the protection reaction is conducted at room temperature for at least 1 hour, notably for at least 2 hours.

Step (b)—Alkynylation

Coupling the protected mannose obtained at step (a) with a compound of formula (II) comprising a terminal alkyne can be performed in the presence of a base and an alkyl-aluminum halide, and optionally a Lewis acid.

In particular, the base is selected among an organolithium reagent $R^bLi$ or a Grignard reagent $R^cMgX^a$ with $R^b$ and/or $R^c$ representing a $(C_1$-$C_6)$alkyl group and $X^a$ representing a halogen.

Preferably, the base is an organolithium reagent, notably n-butyl lithium (nBuLi).

Advantageously, the alkylaluminum halide is a dialkyl-aluminium halide, in particular diethylaluminium chloride ($Et_2AlCl$) or dimethylaluminium chloride ($Me_2AlCl$). Preferably, the alkylaluminum halide is $Et_2AlCl$.

In particular, in addition to the alkylaluminum halide, which is a Lewis acid, step (b) occurs in the presence of at least another Lewis acid. The Lewis acid is preferably selected among $BF_3$, $BCl_3$, $BBr_3$, $TiCl_4$, $PF_5$, $SbF_5$, $SnCl_2$, $SnCl_4$, $ZnCl_2$, aluminium halide or mixture thereof. Advantageously, the Lewis acid is selected among boron trihalide and aluminium halide or mixture thereof. Preferably aluminium halide is chosen among $AlCl_3$ and $AlBr_3$, more preferably it is $AlCl_3$.

Preferably, step (b) is performed in the presence of an alkylaluminum halide and another Lewis acid. More preferably, step (b) is performed in the presence of an alkylaluminum halide and an aluminium halide. Even more preferably, step (b) is performed in the presence of $Et_2AlCl$ $AlCl_3$.

In particular, step (b) is performed in the presence of $AlCl_3$, $Et_2AlCl$ and nBuLi.

Preferably, step (b) is conducted in apolar solvent such as toluene, xylene or dichloroethane. More preferably, step (b) is conducted in a mixture toluene/THF.

In a specific embodiment, step (b) is divided into three sub-steps:

(b1) deprotonation of the compound of formula (II) with a base, (b2) addition of an alkylaluminium halide, preferably diethyl aluminium chloride, (b3) coupling the product obtained at step (a) with the product obtained at step (b2)

in the presence of a Lewis acid, preferably aluminium chloride.

Deprotonation of the compound of formula (II) is preferably performed with a base selected among organolithium reagent or a Grignard reagent, more preferably, with an organolithium reagent, notably n-butyl lithium nBuLi.

Advantageously, addition of the base is carried out at a temperature below −30° C. and the mixture is stirred at 0° C. for at least 10 minutes, in particular at least 20 minutes.

Step (b2) is a transmetallation reaction. Preferably, addition of an alkylaluminium halide to the deprotonated compound obtained at step (b1) is carried out at a temperature below 0° C., more preferably below −20° C., and the mixture is stirred at room temperature for at least 10 minutes.

In particular, step (b3) is performed by adding a Lewis acid and the product obtained at step (a), i.e. the protected mannose, at a temperature below −20° C. and the mixture is stirred at at least 50° C. for at least 10 hours, more preferably, at least 20 hours.

In particular, compounds of formula (I) can be obtained using the following synthetic route:

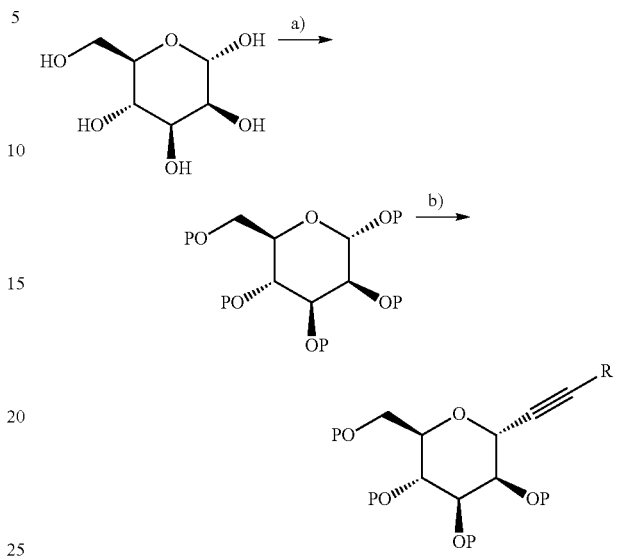

Preferably, compounds of formula (I) can be obtained using the following synthetic route:

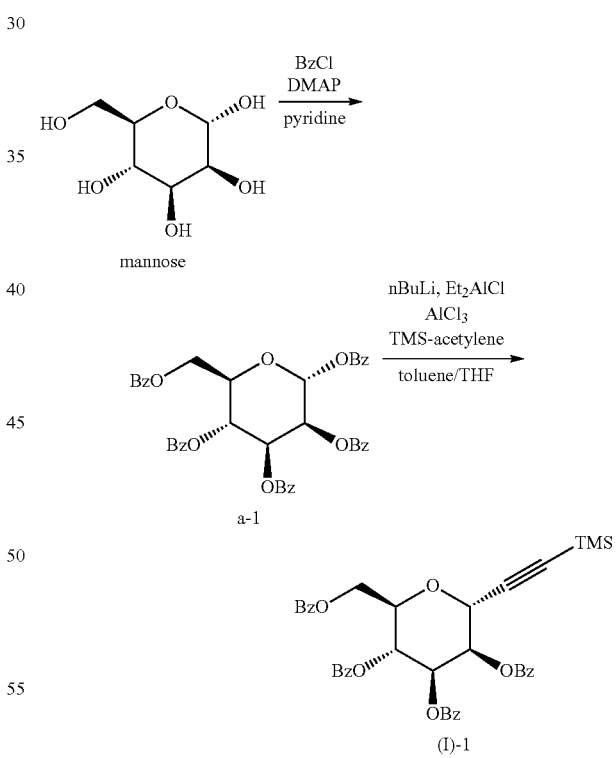

Step (c)—Deprotection of the Terminal Alkyne

In a specific embodiment, when R represents a protective group of a terminal alkyne, step (b) is followed by step (c) deprotecting the terminal alkyne of the compound obtained at step (b) to obtain compound of formula (I) in which R=H.

Deprotecting terminal alkyne is conducted under conditions well known to skilled persons.

In particular, when R is a —SiR²R³R⁴ group, deprotection can occur in the presence of fluoride ion, notably in the presence of potassium fluoride, tetra-n-butyl ammonium fluoride or silver fluoride.

Preferably, step (c) is conducted in a polar solvent such as DMA, DMF, DMSO, THF, dioxane, acetonitrile or NMP.

In particular, compounds of formula (I) can be obtained using the following synthetic route:

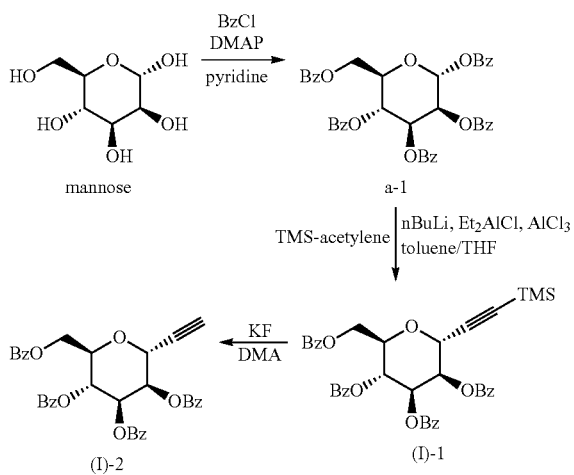

Preparation of Compounds of Formula (III)

The invention also deals with a process to prepare a compound of formula (III):

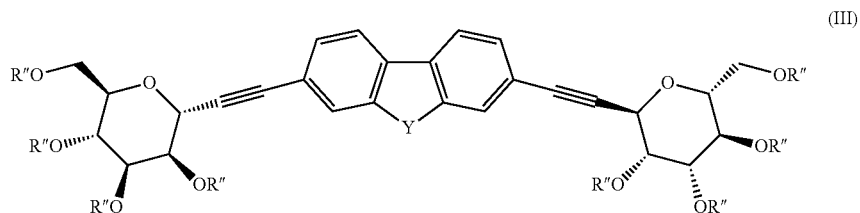

in which
Y represents an atom S, an atom O, a

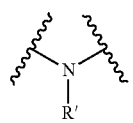

group or a

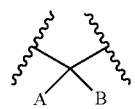

group,
with A and B representing independently of each other a hydrogen a hydroxyl, an amine or a radical selected from a $(C_1$-$C_6)$alkyl and an aryl, said radical being substituted or not by a $(C_1$-$C_6)$alkyl, a 3-8 membered ring cycloalkyl, —OR⁵, —OC(O)R⁵ or —COOR⁵, R⁵ representing a hydrogen or a $(C_1$-$C_6)$alkyl, or A and B form together with the carbon atom to which they are bound a 3-7 membered saturated monocyclic ring having 0, 1 or 2 heteroatoms selected from O, N and S, one or several carbon or nitrogen of the ring being optionally substituted by an oxo, a $(C_1$-$C_6)$alkyl, —OR⁶, —NR⁶R⁷, —SO₂R⁶—C(O)R⁶ or —C(O)OR⁶, with R⁶ and R⁷ representing independently a hydrogen or a radical selected from a $(C_1$-$C_6)$alkyl, an aryl, a heteroaryl, a 3-8 membered ring cycloalkyl and a 3-8 membered ring heterocycloalkyl, said radical being optionally substituted by a $(C_1$-$C_6)$ alkyl, an aryl, a heteroaryl, a 3-8 membered ring cycloalkyl, a 3-8 membered ring heterocycloalkyl, a halogen, —NR⁸R⁹, —CN, —C(O)OR⁸, —C(O)NR⁸R⁹ or —OR⁸, with R⁸ and R⁹ being independently a hydrogen atom or a $(C_1$-$C_6)$ alkyl, or R⁸ and R⁹ form together with the nitrogen to which they are bound a 3-8 membered ring heterocycloalkyl, with R' representing a hydrogen atom or a radical selected from a $(C_1$-$C_6)$ alkyl, an aryl, a 3-8 membered ring cycloalkyl and a 3-8 membered ring heterocycloalkyl, said radical being optionally substituted by a $(C_1$-$C_6)$ alkyl, a 3-8 membered ring cycloalkyl, a 3-8 membered ring heterocycloalkyl, —C(O)OR$^a$, —C(O)NR$^a$R$^b$ or —OR$^a$, with R$^a$ and R$^b$ being independently a hydrogen atom or a $(C_1$-$C_6)$ alkyl optionally substituted by a 3-8 membered ring heterocycloalkyl, or R$^a$ and R$^b$ form together with the nitrogen a 3-8 membered ring heterocycloalkyl, R" represents a hydrogen atom or a protective group of a hydroxyl function which is a —COR¹ group with R¹ representing an aryl or a $(C_1$-$C_6)$alkyl, from mannose, comprising the following steps:

(a)(b) performing steps (a) and (b) to obtain the compound of formula (I) as described in any of the preceding claims;

(c) optionally deprotecting the terminal alkyne of the compound obtained after steps (a)(b) to obtain compound of formula (I) in which R=H;

(d) Sonogashira coupling of the compound obtained at steps (a)(b) or when applicable at step (c) with a compound of the following formula (IV):

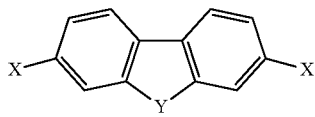

(IV)

in which X is a halogen atom;

(e) optionally deprotecting the hydroxyl groups protected by a group P to obtain compound of formula (III) in which R"=H;

(f) recovering the compound of formula (III) obtained at step (d) or when applicable at step (e).

In an alternative embodiment, step (e) occurs after step (c) and before step (d).

In particular, R" represents a protective group P as described above.

Preferably, the protective group P is a —$COR^1$ group with $R^1$ representing an aryl group, preferably $R^1$ is a phenyl group.

In a first embodiment, Y represents a

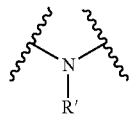

group.

In particular, R' is as described above.

In a second embodiment, Y represents a

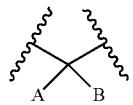

group.

In particular, A and B are as described above.

Advantageously, A and B represent independently of each other a hydrogen, a hydroxyl or a ($C_1$-$C_6$)alkyl substituted or not by a —$OR^5$ group or —$OC(O)R^5$ group, $R^5$ representing a hydrogen or a ($C_1$-$C_6$)alkyl, or A and B form together with the carbon atom to which they are bound a 3-7 membered saturated monocyclic ring having 0, 1 or 2 heteroatoms selected from O, N and S, one or several carbon or nitrogen of the ring being optionally substituted by an oxo, a ($C_1$-$C_6$)alkyl, —$OR^6$, —$NR^6R^7$, —$SO_2R^6$—$C(O)R^6$ or —$C(O)OR^6$, with $R^6$ and $R^7$ representing independently a hydrogen or a radical selected from a ($C_1$-$C_6$)alkyl, an aryl, a heteroaryl, a 3-8 membered ring cycloalkyl and a 3-8 membered ring heterocycloalkyl, said radical being optionally substituted by a ($C_1$-$C_6$) alkyl, an aryl, a heteroaryl, a 3-8 membered ring cycloalkyl, a 3-8 membered ring heterocycloalkyl, a halogen, —$NR^8R^9$, —CN, —$C(O)OR^8$, —$C(O)NR^8R^9$ or —$OR^8$, with $R^8$ and $R^9$ being independently a hydrogen atom or a ($C_1$-$C_6$) alkyl, or $R^8$ and $R^9$ form together with the nitrogen to which they are bound a 3-8 membered ring heterocycloalkyl.

Preferably, the compound of formula (III) is a compound of formula (IIIa)

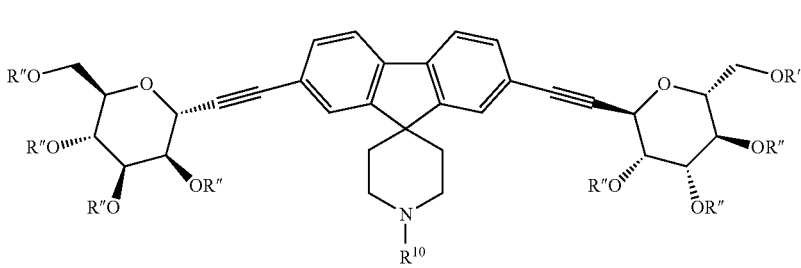

(IIIa)

with $R^{10}$ representing a hydrogen, a ($C_1$-$C_6$)alkyl, —$SO_2R^6$, —$C(O)R^6$ or —$C(O)OR^6$, with $R^6$ and R" being as described above.

Compound (IIIa) is advantageously obtained from compound (IVa)

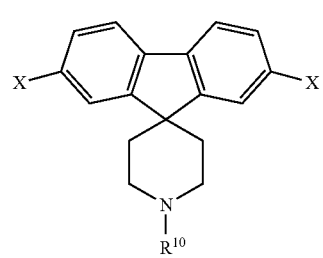

(IVa)

with $R^{10}$ representing a hydrogen, a ($C_1$-$C_6$)alkyl, —$SO_2R^6$, —$C(O)R^6$ or —$C(O)OR^6$, with X being a halogen atom.

Preferably, $R^{10}$ is a —$C(O)R^6$ group with $R^6$ representing an aryl or a ($C_1$-$C_6$)alkyl, preferably $R^6$ is a methyl group.

Step (a), (b) and (c)

Steps (a), (b) and (c) can be performed as described above.

Step (d)—Sonogashira Coupling

Sonogashira coupling of compound of formula (I) with R=H and compound of formula (IV) is conducted under conditions well known to skilled persons.

Preferably, X in compound of formula (IV) is a bromine or an iodine, more preferably, a bromine.

Sonogashira coupling can be performed in the presence of a palladium catalyst, or a system of palladium/copper catalyst.

Some suitable examples of Pd and Pd/Cu catalysts include $Pd(PPh_3)_4$, $Pd(PPh_3)_4$/CuI $PdCl_2$(dppf)/CuI, $PdCl_2(PPh_3)$/CuI.

In particular, Sonogashira coupling occurs in the presence of a base, such as an amine.

Preferably, the amine is trimethylamine (TEA), diisopropylethylamine (DIPEA), piperidine, morpholine or pyridine. More preferably, the base is DIPEA.

Advantageously, Sonogashira coupling is conducted in a polar solvent. In particular, DMSO, DMF, DMA, THF, dioxane, acetonitrile or NMP can be used as solvent.

Preferably, Sonogashira coupling is performed under nitrogen or under argon at a temperature above room temperature, notably above 50° C., for at least 10 hours, preferably at least 20 hours.

In particular, steps (c) and (d) occur in a one-pot process. Thus steps (c) and (d) occur in the same reactor without isolation of the intermediate obtained after step (c). Preferably, steps (c) and (d) occur in the same solvent.

Step (e)—Deprotection of the Hydroxyl Groups of the Mannose Moiety

Compounds of formula (III) with R″ representing a protective group P obtained following step (d) can be subjected to deprotection of the hydroxyl groups of the mannose moiety.

Deprotection of hydroxyl groups protected by a group P is conducted under conditions well known to skilled persons and depends on the protective group.

When P is a —COR$^1$ group, deprotection consists in a saponification. Saponification is well known to skilled persons.

In particular, deprotection occurs in the presence of a base such as a hydroxide or an alkoxide. In particular, the base is an alkoxide, preferably a methoxide, more preferably sodium methoxide.

The reaction can be performed in an alcohol, preferably corresponding to the alkoxide used. In particular, deprotection occurs in methanol.

The reaction can be performed at room temperature for at least 1 hour.

Step (f)—Recovery of Compound of Formula (III)

Compound of formula (III) with R″=H can be purified by recrystallization in an alcohol, preferably isopropanol.

In particular, compounds of formula (III) can be obtained using the following synthesis scheme:

Compound of formula (IIIa) is obtained by Sonogashira coupling of compound of formula (I) and compound of formula (IVa):

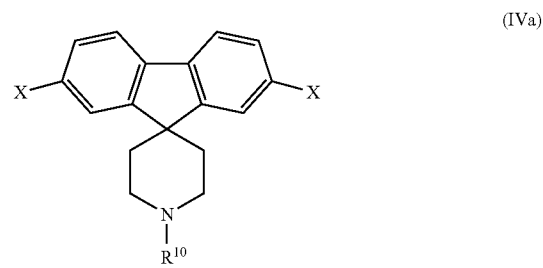

In a specific embodiment, compound of formula (IVa) wherein R$^{10}$ is a —COMe group is obtained from compound of formula (IVa) with R$^{10}$ being a protective group of an amine function different from —COMe, notably a Boc group, by deprotection and acetylation in a one-pot process.

In particular, compound of formula (IVa) is obtained through the following synthetic route:

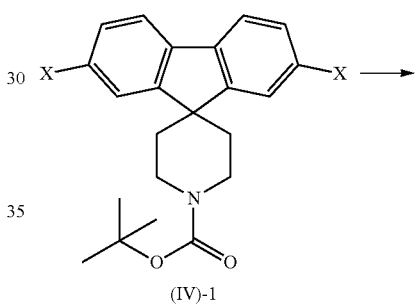

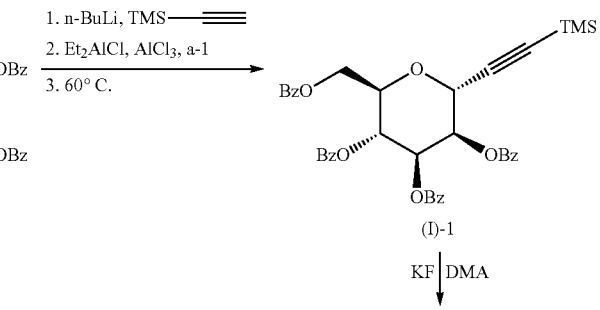

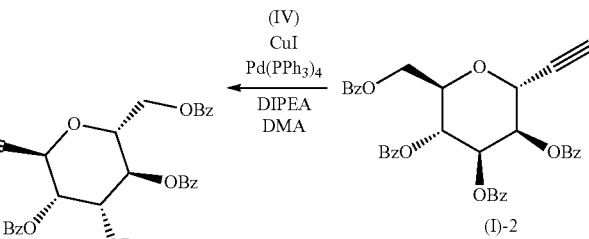

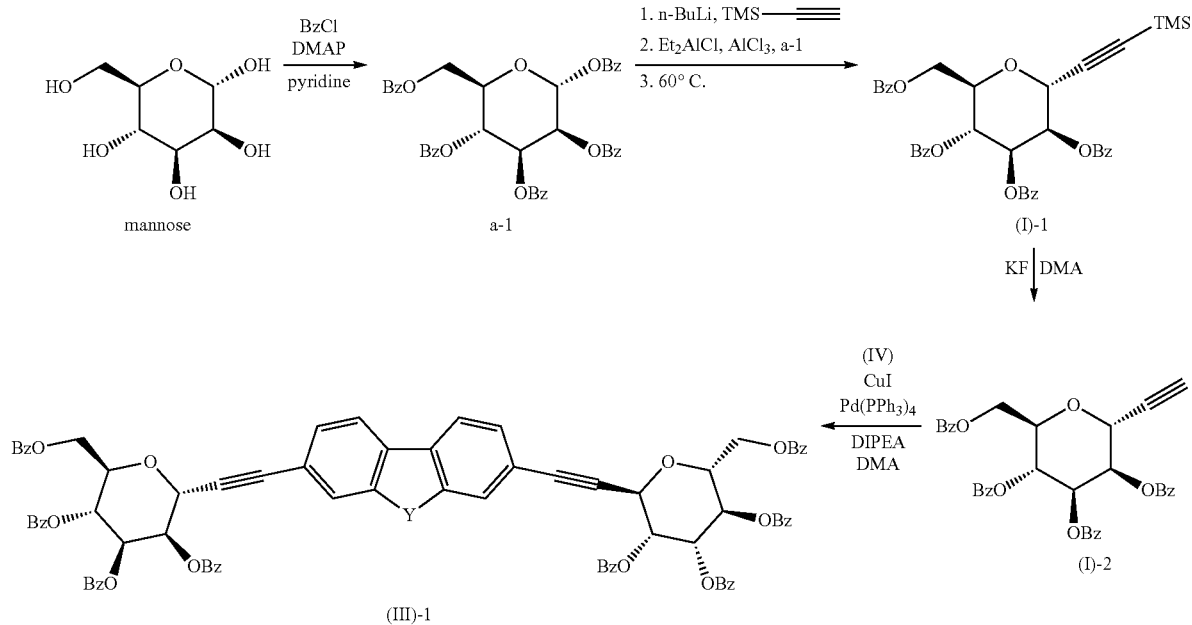

19
-continued
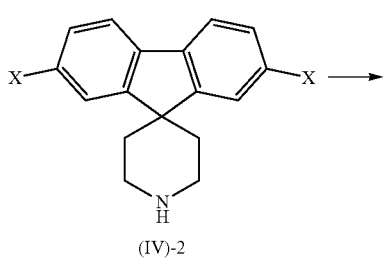
(IV)-2
20
-continued
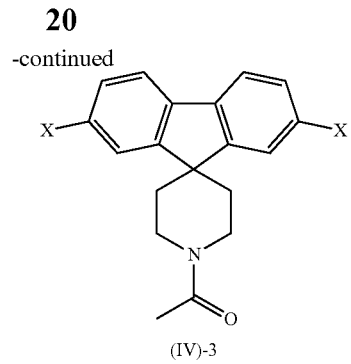
(IV)-3
In one embodiment of the present invention, compounds of formula (IIIa) are prepared with the following synthesis scheme:
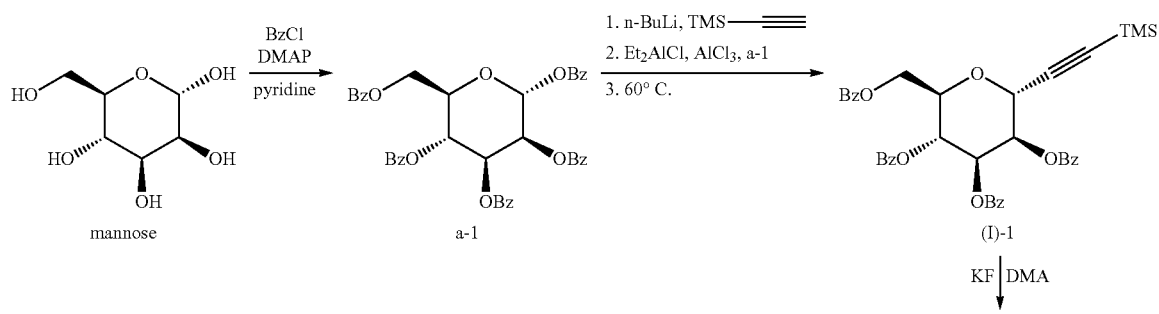
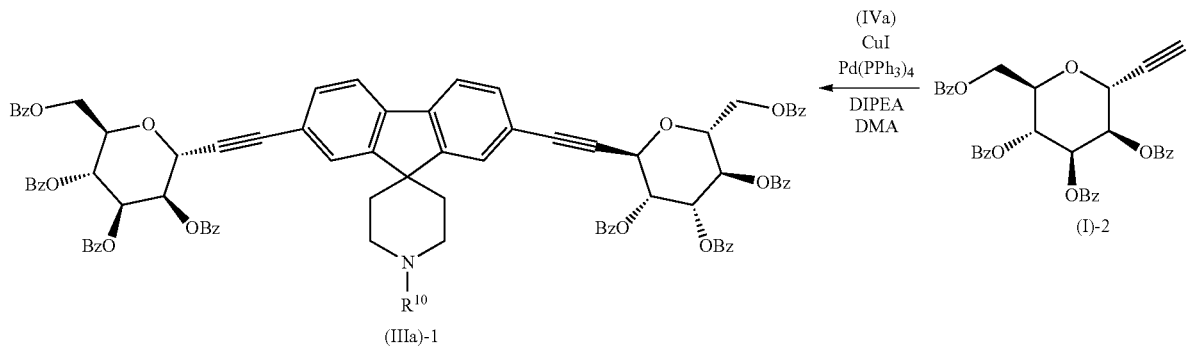
In one embodiment of the present invention, compound of formula (IIIa)-3 is prepared with the following synthetic route:
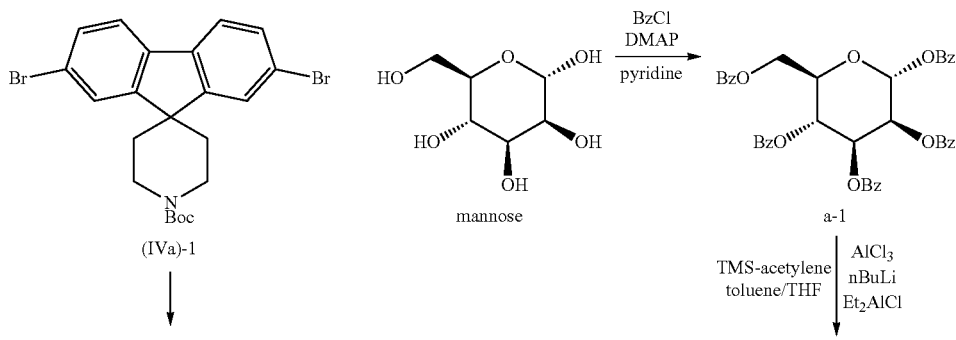

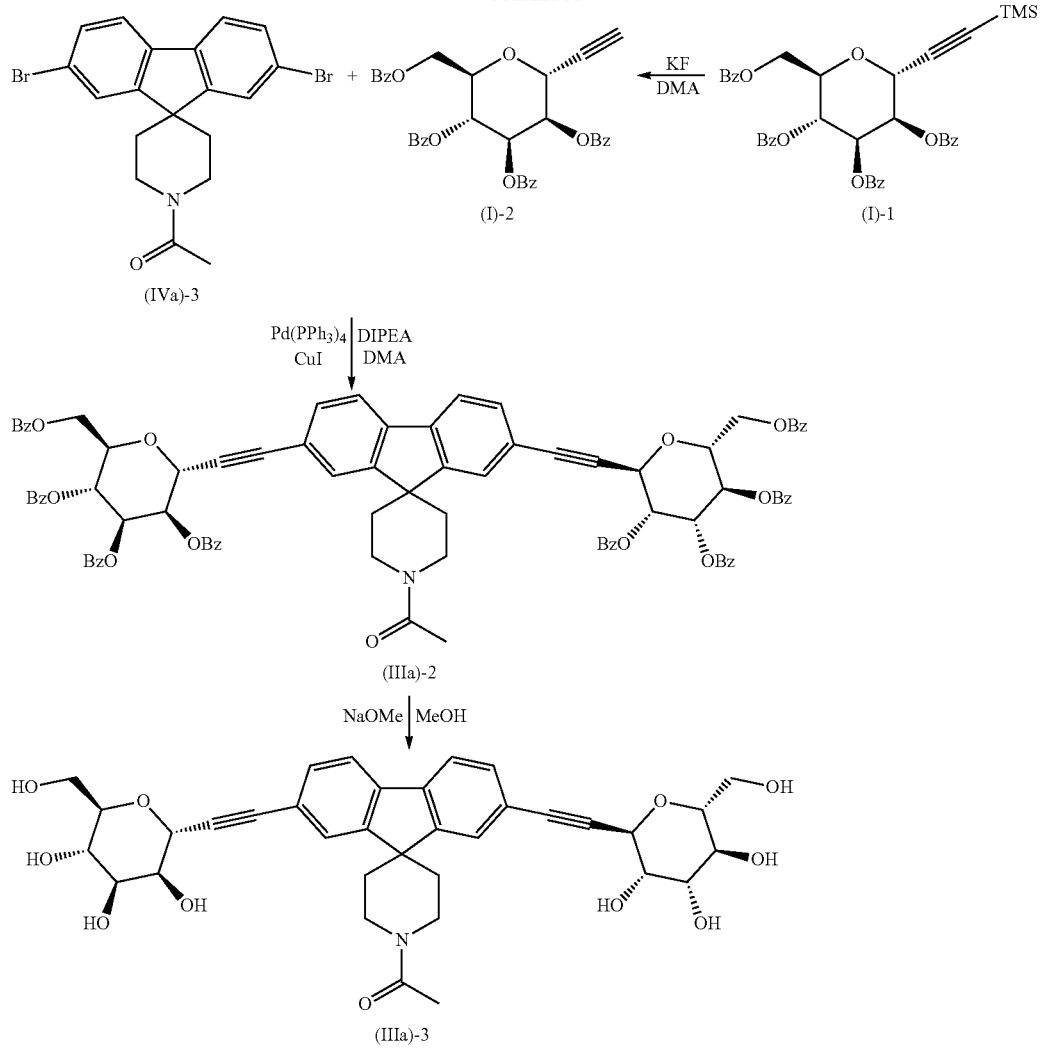

The desired product (IIIa)-3 is obtained with a global yield starting from mannose in the order of 35% to 40%.

Preparation of Compounds of Formula (V)

The invention also deals with a process to prepare a compound of formula (V):

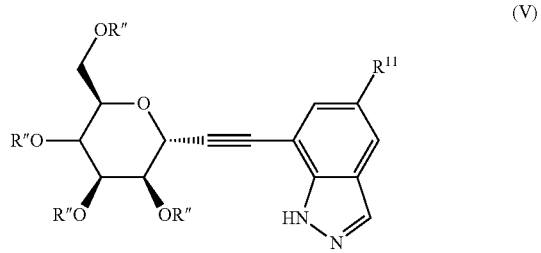

in which
$R^{11}$ represents:
a —$CONR^{12}R^{13}$ group with $R^{12}$ and $R^{13}$ representing independently a hydrogen or a $(C_1$-$C_6)$alkyl or $R^{12}$ and $R^{13}$ form together with the nitrogen a 3-8 membered ring heterocycloalkyl or cycloalkyl, a radical selected from a cycloalkenyl, an aryl and a heteroaryl, said radical being substituted or not by a $(C_1$-$C_6)$ alkyl, an aryl, a heteroaryl, a halogen, —C(O)$OR^a$, —C(O)$NR^aR^b$, —$SO_2R^a$, —$SO_2NR^aR^b$, —$NR^aR^b$, —$OR^a$, —CN or —$NO_2$, with $R^a$ and $R^b$ being independently a hydrogen atom or a $(C_1$-$C_6)$ alkyl, R" represents a hydrogen atom or a protective group of a hydroxyl function which is a —$COR^1$ group with $R^1$ representing an aryl or a $(C_1$-$C_6)$alkyl, from mannose, comprising the following steps:
(a)(b) performing steps (a) and (b) to obtain the compound of formula (I) as described in any of the preceding claims;
(c) optionally deprotecting the terminal alkyne of the compound obtained after steps (a)(b) to obtain compound of formula (I) in which R=H;
(d) Sonogashira coupling of the compound obtained at steps (a)(b) or when applicable at step (c) with a compound of the following formula (VI):

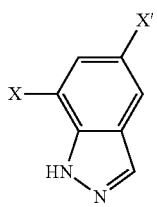

(VI)

in which X is a halogen atom and X' is a halogen or a radical $R^{11}$;

(e) optionally deprotecting the hydroxyl groups protected by a group P to obtain compound of formula (V) in which R"=H;

(f) recovering the compound of formula (V) obtained at step (d) or when applicable at step (e).

In an alternative embodiment, step (e) occurs after step (c) and before step (d).

In particular, $R^{11}$ represents a radical selected from an aryl and a heteroaryl, said radical being substituted or not by a ($C_1$-$C_6$) alkyl, an aryl, a heteroaryl, a halogen, —C(O)O$R^a$, —C(O)N$R^a R^b$, —SO$_2 R^a$, —SO$_2$N$R^a R^b$, —N$R^a R^b$, —O$R^a$, —CN or —NO$_2$, with $R^a$ and $R^b$ being independently a hydrogen atom or a ($C_1$-$C_6$) alkyl. More preferably, $R^{11}$ represents a heteroaryl substituted or not by a ($C_1$-$C_6$) alkyl, an aryl, a heteroaryl, a halogen, —C(O)O$R^a$, —C(O)N$R^a R^b$, —SO$_2 R^a$, —SO$_2$N$R^a R^b$, —N$R^a R^b$, —O$R^a$, —CN or —NO$_2$, with $R^a$ and $R^b$ being independently a hydrogen atom or a ($C_1$-$C_6$) alkyl. Even more preferably, $R^{11}$ represents a pyridinone substituted or not by a ($C_1$-$C_6$) alkyl group.

In a specific embodiment, the compound of formula (V) is a compound of formula (Va)

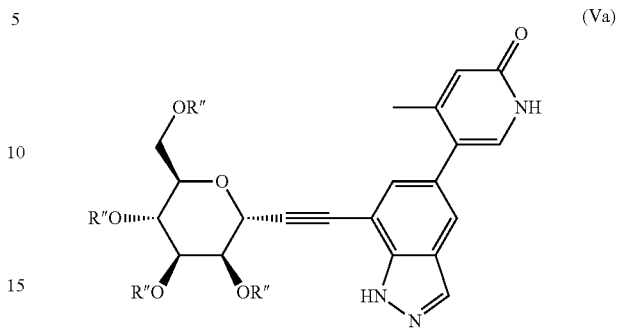

Step (a), (b), (c), (e) and (f)
Steps (a), (b) and (c) can be performed as described above.
Step (d)—Sonogashira Coupling
Steps (d) can be performed as described above.
In a specific embodiment, when $R^{11}$ represents an aryl or a heteroaryl, then X' represents advantageously a halogen.
In this embodiment, an additional step (d') between step (d) and step (e) can be performed.
Step (d') is a Suzuki coupling between the product obtained at step (d) and an aryl- or heteroaryl-boron derivative.
Suzuki coupling is conducted under condition known to skilled persons.
The boron derivative can be a boronic acid derivative, a boronic ester derivative or a trifluoroborate derivative. The radical aryl or heteroaryl of the aryl- or heteroaryl-boron derivative correspond to the group $R^{11}$. Thus, when the boron derivative is a boronic acid derivative, its formula is $R^{11}$—B(OH)$_2$.
Suzuki coupling can be performed in the presence of a palladium catalyst such as Pd(PPh$_3$)$_4$.
In particular, Suzuki coupling occurs in the presence of a base, such as a carbonate, an acetate or an amine.
In particular, compounds of formula (V) can be obtained using the following synthesis scheme

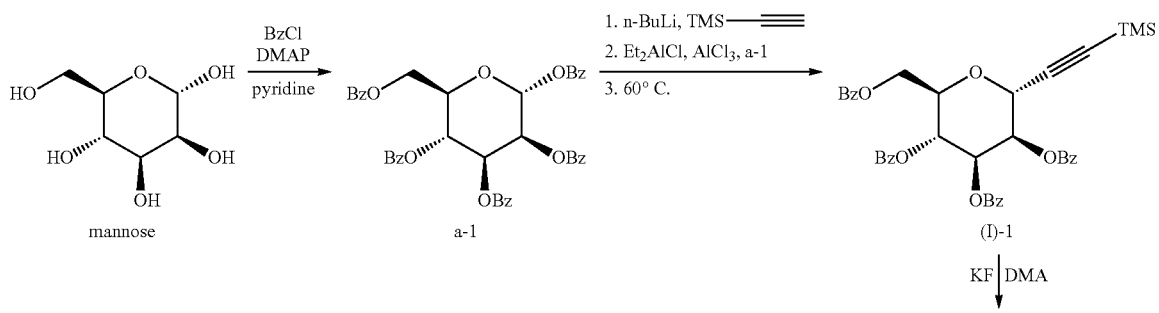

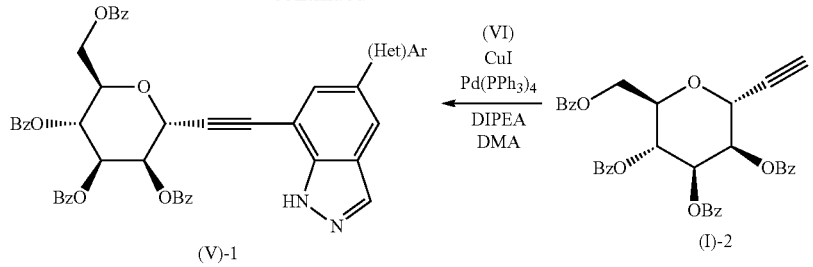
In one embodiment of the present invention, compounds of formula (V) are prepared with the following synthesis scheme:
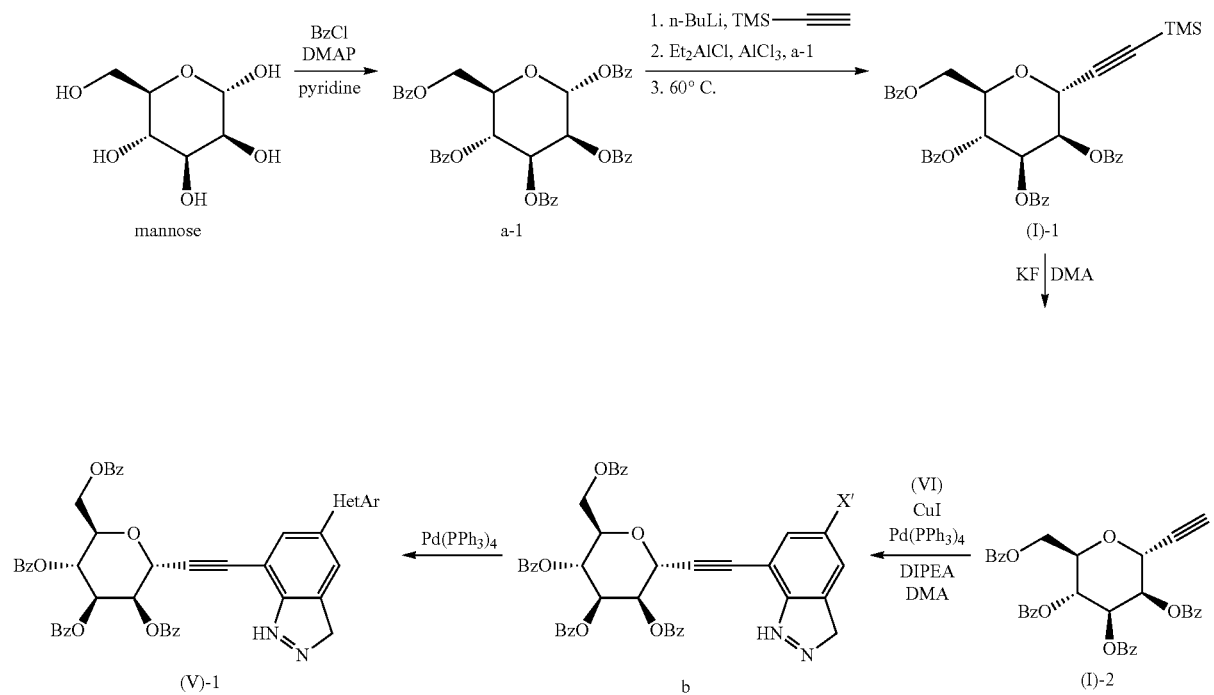
Compound of Formula (IIIa)
According to the present invention, in the compound of the following formula (IIIa):
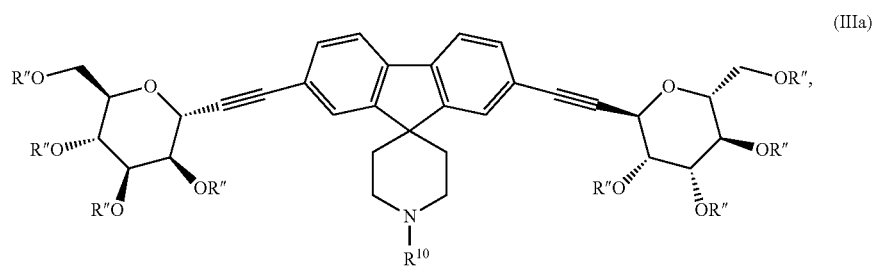

R[10] represents advantageously a —C(O)R[6] group with R[6] representing an aryl or a (C₁-C₆)alkyl, preferably R[6] is a methyl group.

Preferably, R" represents —COR[1] group with R[1] being an aryl, such as a phenyl, or a (C₁-C₆)alkyl, such as a methyl. More preferably, R" represents a benzoyl group of formula —COPh, wherein Ph is the abbreviation for the phenyl group.

According to a preferred embodiment, compound of formula (IIIa) is the compound of the following formula (IIIa-2):

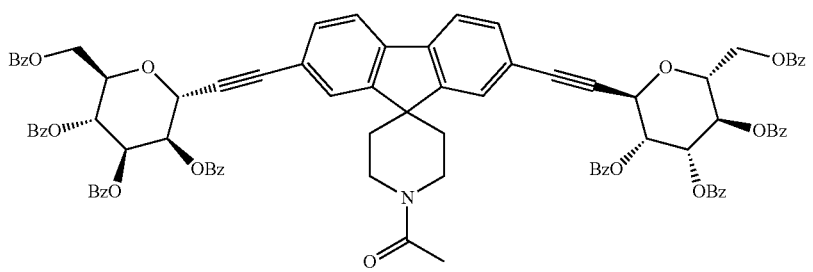

(IIIa)-2

Examples

Abbreviation

Bz benzoyl
n-BuLi n-butyl lithium
MTBE methyl tert-butyl ether
DMA dimethylacetamide
THF tetrahydrofuran

Preparation of Compound a-1

D-mannose (1.0 equiv.) and dimethylaminopyridine (0.1 equiv.) are dissolved in pyridine (20 vol). Benzoyl chloride (8.0 equiv.) is added at −15° C. The reaction mixture is stirred at room temperature for 2 hours. Ethyl acetate is added. The mixture is cooled to −15° C. and a solution of hydrochloric acid (3 M) is added until pH<7. The organic phase is isolated and washed with a solution of sodium bicarbonate, and then a solution of sodium chloride. The organic phase is then dried on anhydrous sodium sulfate and evaporated under reduced pressure. Ethanol is added to precipitate compound a-1. The mixture is filtered and the filter cake is washed with ethanol. The filter cake is dried under vacuum and compound a-1 is obtained as a white solid with a purity above 95% by HPLC and a yield ranging from 70 to 90%. 1H NMR (400 MHz, DMSO) δ 7.95-8.25 (m, 8H), 7.36-7.82 (m, 17H), 6.58 (s, 1H), 5.91-6.17 (m, 3H), 4.82-4.84 (m, 1H), 4.52-4.67 (m, 2H). ESI-MS m/z calc. 700.1, found (M+Na)+: 723.4.

Preparation of Compound (I)-1 n-BuLi (2.5 M in hexanes, 2.0 equiv.) is added to a solution of trimethylsilyl acetylene (2.1 equiv.) in toluene (6.6 vol.) at a temperature below −30° C. The reaction mixture is stirred at 0° C. for 20 min. The mixture is cooled and diethyl aluminium chloride is added at a temperature below −20° C. The reaction is stirred at room temperature for 10 min. The mixture is cooled at −30° C. and THF (2.0 equiv.), aluminium chloride (2.0 equiv.) and compound a-1 (1.0 equiv.) are successively added. The reaction mixture is stirred at 60° C. for 20 hours. The mixture is cooled at −30° C. and MTBE (10 vol.) and a solution of hydrochloric acid (2 M) are added successively. The organic phase is isolated and washed with a solution of sodium bicarbonate, and then a solution of sodium chloride. The organic phase is then dried on anhydrous sodium sulfate. DMA (2.9 vol.) is added. The organic solvents except DMA are evaporated. Compound (1)-1 in solution in DMA is ready for next step at a purity>60% and an estimate yield ranging from 80 to 90%. 1H NMR (400 MHz, DMSO) δ 7.40-8.20 (m, 20H), 5.90-6.05 (m, 2H), 5.74-5.79 (m, 1H), 5.30-5.33 (m, 1H), 4.53-4.72 (m, 3H), 0.35 (s, 9H). ESI-MS m/z calc. 676.2, found (M+Na)+: 699.5.

Preparation of Compound (IVa)-3

To a solution of compound (IVa)-1 (1 equiv.) in acetic acid is added acetic anhydride (2.0 equiv.) and acetyl chloride (2.0 equiv.) at room temperature. The reaction mixture is stirred at 100° C. for 7 hours. The reaction mixture is cooled at room temperature and stirred for 6 hours. Sodium acetate (2.5 equiv.) is added followed by water at room temperature and stirred for 3 hours. The reaction mixture is filtered. The filer cake is washed with water and dried under vacuum. Compound (IVa)-3 is obtained with a yield ranging from 85 to 100%. 1H NMR (400 MHz, DMSO) δ 8.01 (s, 2H), 7.86-7.89 (d, 2H, J=8.0 Hz), 7.59-7.62 (d, 2H, J=8.0 Hz), 3.80-3.85 (m, 4H), 2.12 (s, 3H), 1.73-1.90 (m, 4H). ESI-MS m/z calc. 432.9, found (M+Na)+: 456.0.

Preparation of Compound (IIIa)-2

To a solution of compound (1)-1 (2.5 equiv.) in DMA is added compound (IVa)-3 (1.0 equiv.) and potassium fluoride (8.0 equiv.). The reaction mixture is stirred under vacuum at room temperature for 30 min. N,N-diisopropylethylamine (4.0 equiv.) is added. Nitrogen is bubbled into the reaction mixture for 30 min. The reaction mixture is heated at 50° C. and tetrakis(triphenylphosphine)palladium (0.05 equiv.) and copper iodide (0.1 equiv.) are added successively. The reaction mixture is stirred at 60° C. for 24 hours. The reaction mixture is cooled at 10° C. and acetic acid (8.0 equiv.), methanol (12 vol.) and N-acetyl-cysteine (2.0 equiv.) are added successively. The reaction mixture is stirred at 30° C. for 48 hours. The reaction mixture is filtered. The filer cake is washed with methanol and dried under vacuum. Compound (IIIa)-2 is obtained as a white solid with a purity above 85 to 90% by HPLC and a yield ranging from 85 to 95%. 1H NMR (400 MHz, DMSO) δ 7.37-8.17 (m, 46H), 6.00-6.12 (m, 4H), 5.91-5.92 (m, 2H), 5.57-5.58 (m, 2H), 4.72-4.84 (m, 4H), 4.59-4.62 (m, 2H), 3.95-4.00 (m, 4H), 2.14 (s, 3H), 1.88-1.89 (m, 4H). ESI-MS m/z calc. 1481.5, found (M+Na)+: 1505.6.

Preparation of Compound (IIIa)-3

To a solution of compound (IIIa)-2 (1.0 equiv.) in THE are added successively methanol and sodium methoxide, 25% in methanol (1.1 equiv.) at a temperature below 20° C. The reaction mixture is stirred at room temperature for 16 hours. Isopropanol is added. The reaction mixture is stirred for 2 hours at room temperature. The reaction mixture is filtered. The filter cake is washed with isopropanol and dried under vacuum. Compound (IIIa)-3 is obtained as a brown solid with a purity above 95% by HPLC and a yield ranging from 90 to 100%. 1H NMR (400 MHz, DMSO) δ 7.93-7.95 (d, 2H, J=8.0 Hz), 7.85 (s, 2H), 7.50-7.52 (d, 2H, J=8.0 Hz), 4.98-4.99 (d, 2H), 4.72-4.82 (m, 6H), 4.49-4.52 (m, 2H), 3.85-3.95 (m, 6H), 3.71-3.80 (m, 4H), 3.42-3.61 (m, 6H), 2.13 (s, 3H). ESI-MS m/z calc. 649.3, found (M+Na)+: 672.4.

The invention claimed is:

1. A process to prepare a compound of the following formula (I):

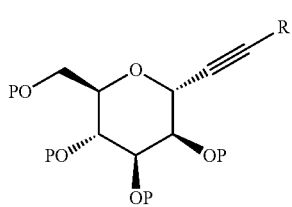

in which

P represents a protective group of a hydroxyl function which is a —COR$^1$ group with R$^1$ representing
an aryl or a (C$_1$-C$_6$)alkyl,
R represents a hydrogen atom or a protective group of a terminal alkyne,
from mannose, comprising the following steps:
(a) protecting the 5 hydroxyl groups of the mannose by a protective group P;
(b) coupling the protected mannose obtained at step (a) with a compound of the following formula (II)

2. The process according to claim 1, wherein the protective group P is a —COR$^1$ group with R$^1$ representing an aryl group.

3. The process according to claim 1, wherein R is a —SiR$^2$R$^3$R$^4$ group with R$^2$, R$^3$ and R$^4$ representing independently from each other a (C$_1$-C$_6$)alkyl group or a biphenyl group.

4. The process according to claim 1, wherein step b) is performed in the presence of a base, an alkylaluminum halide and optionally a Lewis acid.

5. The process according to claim 1, wherein step (b) is divided into three sub-steps:
(b1) deprotonation of the compound of formula (II) with a base,
(b2) addition of an alkylaluminium halide,
(b3) coupling the product obtained at step (a) with the product of step (b2) in the presence of a Lewis acid.

6. A process to prepare a compound of formula (III):

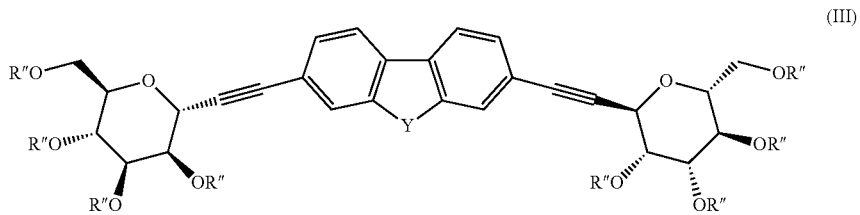

in which

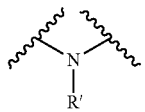

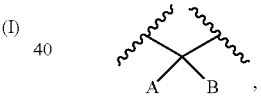

Y represents a group or a group
with A and B representing independently of each other a hydrogen, a hydroxyl, an amine or a radical selected from a (C$_1$-C$_6$)alkyl and an aryl, said radical being substituted or not by a (C$_1$-C$_6$)alkyl, a 3-8 membered ring cycloalkyl, —OR$^5$, —OC(O)R$^5$ or —COOR$^5$, R$^5$ representing a hydrogen or a (C$_1$-C$_6$)alkyl,
or A and B form together with the carbon atom to which they are bound a 3-7 membered saturated monocyclic ring having 0, 1 or 2 heteroatoms selected from O, N and S, one or several carbon or nitrogen of the ring being optionally substituted by an oxo, a (C$_1$-C$_6$)alkyl, —OR$^6$, —NR$^6$R$^7$, —SO$_2$R$^6$ —C(O)R$^6$ or —C(O)OR$^6$, with R$^6$ and R$^7$ representing independently a hydrogen or a radical selected from a (C$_1$-C$_6$)alkyl, an aryl, a heteroaryl, a 3-8 membered ring cycloalkyl and a 3-8 membered ring heterocycloalkyl, said radical being optionally substituted by a (C$_1$-C$_6$) alkyl, an aryl, a heteroaryl, a 3-8 membered ring cycloalkyl or a 3-8 membered ring heterocycloalkyl, a halogen, —NR$^8$R$^9$, —CN, —C(O)OR$^8$, —C(O)NR$^8$R$^9$ or —OR$^8$, with R$^8$ and R$^9$ being independently a hydrogen atom or a (C$_1$-C$_6$) alkyl, or R$^8$ and R$^9$ form together with the nitrogen to which they are bound a 3-8 membered ring heterocycloalkyl, with R' representing a hydrogen atom or a radical selected from a ($C_1$-$C_6$) alkyl, an aryl, a 3-8 membered ring cycloalkyl and a 3-8 membered ring heterocycloalkyl, said radical being optionally substituted by a ($C_1$-$C_6$) alkyl, a 3-8 membered ring cycloalkyl, a 3-8 membered ring heterocycloalkyl, —C(O)O$R^a$, —C(O)N$R^a R^b$ or —O$R^a$, with $R^a$ and $R^b$ being independently a hydrogen atom or a ($C_1$-$C_6$) alkyl optionally substituted by a 3-8 membered ring heterocycloalkyl, or $R^a$ and $R^b$ form together with the nitrogen a 3-8 membered ring heterocycloalkyl, R" represents a hydrogen atom or a protective group of a hydroxyl function which is a —CO$R^1$ group with $R^1$ representing an aryl or a ($C_1$-$C_6$)alkyl, from mannose, comprising the following steps:
(a) protecting the 5 hydroxyl groups of the mannose by a protective group P;
(b) coupling the protected mannose obtained at step (a) with a compound of the following formula (II)

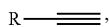
(II)

R represents a hydrogen atom or a protective group of a terminal alkyne;
(c) optionally deprotecting the terminal alkyne of the compound obtained after steps (a)(b) to obtain compound of formula (I) in which R=H;
(d) Sonogashira coupling of the compound obtained at steps (a)(b) or when applicable at step (c) with a compound of the following formula (IV):

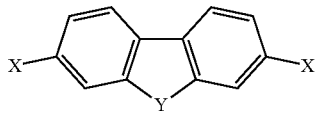
(IV)

in which X is a halogen atom;
(e) optionally deprotecting the hydroxyl groups protected by a group P to obtain compound of formula (III) in which R"=H;
(f) recovering the compound of formula (III) obtained at step (d) or when applicable at step (e).

7. The process according to claim 6, wherein the compound of formula (III) is a compound of formula (IIIa)

with $R^{10}$ representing a hydrogen, a ($C_1$-$C_6$)alkyl, —SO$_2 R^6$, —C(O)$R^6$ or —C(O)O$R^6$, $R^6$ representing a hydrogen or a radical selected from a ($C_1$-$C_6$)alkyl, an aryl, a heteroaryl, a 3-8 membered ring cycloalkyl and a 3-8 membered ring heterocycloalkyl, said radical being optionally substituted by a ($C_1$-$C_6$) alkyl, an aryl, a heteroaryl, a 3-8 membered ring cycloalkyl or a 3-8 membered ring heterocycloalkyl, a halogen, —N$R^8 R^9$, —CN, —C(O)O$R^8$, —C(O)N$R^8 R^9$ or —O$R^8$, with $R^8$ and $R^9$ being independently a hydrogen atom or a ($C_1$-$C_6$) alkyl, or $R^8$ and $R^9$ form together with the nitrogen to which they are bound a 3-8 membered ring heterocycloalkyl, R' representing a hydrogen atom or a radical selected from a ($C_1$-$C_6$) alkyl, an aryl, a 3-8 membered ring cycloalkyl and a 3-8 membered ring heterocycloalkyl, said radical being optionally substituted by a ($C_1$-$C_6$) alkyl, a 3-8 membered ring cycloalkyl, a 3-8 membered ring heterocycloalkyl, C(O)O$R^a$, —C(O)N$R^a R^b$ or —O$R^a$, with $R^a$ and $R^b$ being independently a hydrogen atom or a ($C_1$-$C_6$) alkyl optionally substituted by a 3-8 membered ring heterocycloalkyl, or $R^a$ and $R^b$ form together with the nitrogen a 3-8 membered ring heterocycloalkyl, and R" represents a hydrogen atom or a protective group of a hydroxyl function which is a —CO$R^1$ group with $R^1$ representing an aryl or a ($C_1$-$C_6$)alkyl.

8. The process according to claim 7, wherein $R^{10}$ is a —C(O)$R^6$ group with $R^6$ representing an aryl or a ($C_1$-$C_6$) alkyl.

9. The process according to claim 6, wherein steps (c) and (d) occur in a one-pot process.

10. The process according to claim 7, wherein compound of formula (IVa)

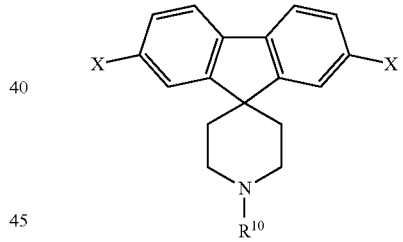
(IVa)

wherein $R^{10}$ is a —COMe group is obtained from compound of formula (IVa) with $R^{10}$ being a protective group of an

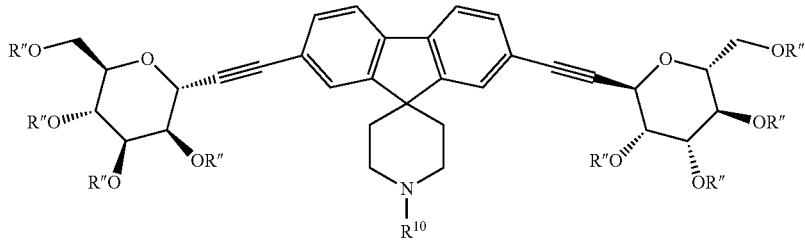
(IIIa)

amine function different from —COMe by deprotection and acetylation in a one-pot process.

11. A process to prepare a compound of formula (V):

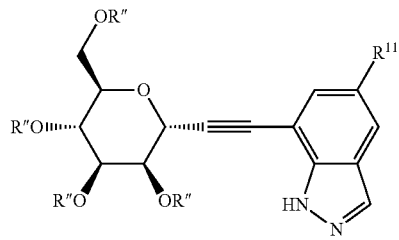

in which

R$^{11}$ represents:
- a —CONR$^{12}$R$^{13}$ group with R$^{12}$ and R$^{13}$ representing independently a hydrogen, a (C$_1$-C$_6$)alkyl or R$^{12}$ and R$^{13}$ form together with the nitrogen a 3-8 membered ring heterocycloalkyl or cycloalkyl
- a radical selected from a cycloalkenyl, an aryl and a heteroaryl, said radical being substituted or not by a (C$_1$-C$_6$) alkyl, an aryl, a heteroaryl, a halogen, —C(O)OR$^a$, —C(O)NR$^a$R$^b$, —SO$_2$R$^a$, —SO$_2$NR$^a$R$^b$, —NR$^a$R$^b$, —OR$^a$, —CN or —NO$_2$, with R$^a$ and R$^b$ being independently a hydrogen atom or a (C$_1$-C$_6$) alkyl, R" represents a hydrogen atom or a protective group of a hydroxyl function which is a —COR$^1$ group with R$^1$ representing an aryl or a (C$_1$-C$_6$)alkyl, from mannose, comprising the following steps:
(a) protecting the 5 hydroxyl groups of the mannose by a protective group P;
(b) coupling the protected mannose obtained at step (a) with a compound of the following formula (II)

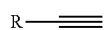 (II)

R represents a hydrogen atom or a protective group of a terminal alkyne;
(c) optionally deprotecting the terminal alkyne of the compound obtained after steps (a)(b) to obtain compound of formula (I) in which R=H;
(d) Sonogashira coupling of the compound obtained at steps (a)(b) or when applicable at step (c) with a compound of the following formula (VI):

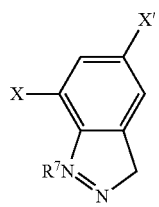

in which X is a halogen atom and X' is a halogen or a radical R$^{11}$;
(e) optionally deprotecting the hydroxyl groups protected by a group P to obtain compound of formula (V) in which R"=H;
(f) recovering the compound of formula (V) obtained at step (d) or when applicable at step (e).

12. The process according to claim 11, wherein R$^{11}$ is a pyridinone substituted or not by a (C$_1$-C$_6$) alkyl.

13. The process according to claim 11, wherein the compound of formula (V) is a compound of formula (Va)

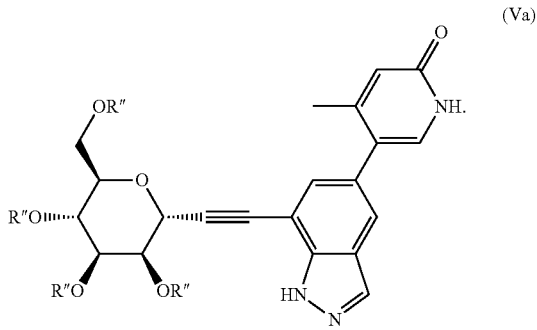

14. The process according to claim 11, wherein steps (c) and (d) occur in a one-pot process.

15. The process according to claim 2, wherein R$^1$ is a phenyl group.

16. The process according to claim 3, wherein R$^2$, R$^3$ and R$^4$ represent a methyl group.

17. The process according to claim 4, wherein step b) is performed in the presence of n-butyl lithium, diethyl aluminium chloride and aluminium chloride.

18. The process according to claim 7, wherein the compound of formula

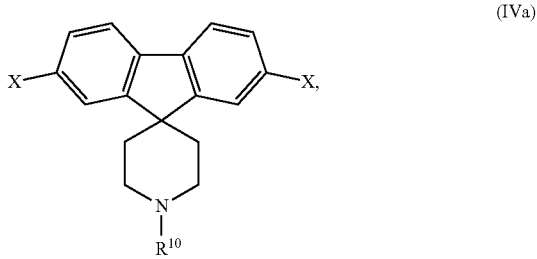

(IIIa) is obtained from compound (IVa) with R$^{10}$ representing a hydrogen, a (C$_1$-C$_6$)alkyl, —SO$_2$R$^6$, —C(O)R$^6$ or —C(O)OR$^6$, R$^6$ representing a hydrogen or a radical selected from a (C$_1$-C$_6$)alkyl, an aryl, a heteroaryl, a 3-8 membered ring cycloalkyl and a 3-8 membered ring heterocycloalkyl, said radical being optionally substituted by a (C$_1$-C$_6$) alkyl, an aryl, a heteroaryl, a 3-8 membered ring cycloalkyl or a 3-8 membered ring heterocycloalkyl, a halogen, —NR$^8$R$^9$, —CN, —C(O)OR$^8$, —C(O)NR$^8$R$^9$ or —OR$^8$, with R$^8$ and R$^9$ being independently a hydrogen atom or a (C$_1$-C$_6$) alkyl, or R$^8$ and R$^9$ form together with the nitrogen to which they are bound a 3-8 membered ring heterocycloalkyl, R' representing a hydrogen atom or a radical selected from a (C$_1$-C$_6$) alkyl, an aryl, a 3-8 membered ring cycloalkyl and a 3-8 membered ring heterocycloalkyl, said radical being optionally substituted by a (C$_1$-C$_6$) alkyl, a 3-8 membered ring cycloalkyl, a 3-8 membered ring heterocycloalkyl,—C(O)OR$^a$, —C(O)NR$^a$R$^b$ or —0R$^a$, with R$^a$ and R$^b$ being independently a hydrogen atom or a (C$_1$-C$_6$) alkyl optionally substituted by a 3-8 membered ring heterocycloalkyl, or $R^a$ and $R^b$ form together with the nitrogen a 3-8 membered ring heterocycloalkyl, R" represents a hydrogen atom or a protective group of a hydroxyl function which is a —$COR^1$ group with $R^1$ representing an aryl or a $(C_1$-$C_6)$alkyl, and X representing a halogen atom.

19. The process according to claim 8, wherein $R^6$ is a methyl group.

* * * * *